United States Patent
Friddle et al.

(10) Patent No.: US 6,448,388 B1
(45) Date of Patent: Sep. 10, 2002

(54) HUMAN PROTEASES AND POLYNUCLEOTIDES ENCODING THE SAME

(75) Inventors: Carl Johan Friddle, The Woodlands; Erin Hilbun, Houston, both of TX (US)

(73) Assignee: Lexicon Genetics Incorporated, The Woodlands, TX (US)

(*) Notice: Subject to any disclaimer, the term of this patent is extended or adjusted under 35 U.S.C. 154(b) by 0 days.

(21) Appl. No.: 09/930,872

(22) Filed: Aug. 15, 2001

Related U.S. Application Data

(60) Provisional application No. 60/225,852, filed on Aug. 16, 2000.

(51) Int. Cl.$^7$ .............................. C12N 9/64; C12N 15/57

(52) U.S. Cl. ...................... 536/23.2; 435/226; 435/219

(58) Field of Search ................................ 435/219, 226; 536/23.2

(56) References Cited

U.S. PATENT DOCUMENTS

| | | | |
|---|---|---|---|
| 4,215,051 A | 7/1980 | Schroeder et al. | 260/346 |
| 4,376,110 A | 3/1983 | David et al. | 436/513 |
| 4,594,595 A | 6/1986 | Struckman | 343/770 |
| 4,631,211 A | 12/1986 | Houghten | 428/35 |
| 4,689,405 A | 8/1987 | Frank et al. | 536/27 |
| 4,713,326 A | 12/1987 | Dattagupta et al. | 435/6 |
| 4,873,191 A | 10/1989 | Wagner et al. | 435/172.3 |
| 4,946,778 A | 8/1990 | Ladner et al. | 435/69.6 |
| 5,252,743 A | 10/1993 | Barrett et al. | 548/303.7 |
| 5,424,186 A | 6/1995 | Fodor et al. | 435/6 |
| 5,445,934 A | 8/1995 | Fodor et al. | 435/6 |
| 5,459,127 A | 10/1995 | Felgner et al. | 514/7 |
| 5,556,752 A | 9/1996 | Lockhart et al. | 435/6 |
| 5,700,637 A | 12/1997 | Southern | 435/6 |
| 5,744,305 A | 4/1998 | Fodor et al. | 435/6 |
| 5,830,721 A | 11/1998 | Stemmer et al. | 435/172.1 |
| 5,837,458 A | 11/1998 | Minshull et al. | 435/6 |
| 5,869,336 A | 2/1999 | Meyer et al. | 435/348 |
| 5,877,397 A | 3/1999 | Lonberg et al. | 800/2 |
| 5,948,767 A | 9/1999 | Scheule et al. | 514/44 |
| 6,075,181 A | 6/2000 | Kucherlapati et al. | 800/25 |
| 6,110,490 A | 8/2000 | Thierry | 424/450 |
| 6,150,584 A | 11/2000 | Kucherlapati et al. | 800/18 |

OTHER PUBLICATIONS

Hurskainen TL, Hirohata S, Seldin MF, Apte SS. (1999) ADAM-TS5, and ADAM T-S6, and ADAM-TS7, novel members of a new family of zinc metalloproteases. General features and genomic distribution of the ADAM-TS family. J Biol Chem.;274(36):25555-63.*

Sequence alignment SEQ ID No.: 4 with AF140675, ADAM-TS7.*

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987 "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–434.

Gu et al, 1994, "Deletion of DNA Polymerase β Gene Segment in T Cells Using Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(5):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promter mutations in lpp gene of *Escherichia coli*", Nucleic Acids Research 13(9):3101–3110.

Janknecht et al, 1991, "Rapid and efficient purification of native histidine–tagged protein expressed by recombinant Avaccinoa virus", PNAS 88:8972–8976.

Kohler & Milstein, 1975, "Continuous cultures of fused cells secreting antibody of prdefined specificity", Nature 256:495–497.

Lasko et al, 1992, "Targeted oncogene activation by site–specific reombination in transgenic mice", Proc. Natl. Acad. Sci. USA 89:6232–6236.

Lavitrano et al, 1989, "Sperm Cells ad Vectors for Introducing Froeign DNA into Eggs: Genetic Transformation of Mice", Cell 57:717–723.

Lo, 1983, "Transformation by Iontophoretic Miroinjection of DNA: Multiple Integrations without Tandem Insertions", Mol. & Cell Bioilopy 3(10):1803–1814.

Logan et al, 1984, "Adenovirus tripartite leader sequence enchances translation of mRNAs late after infection", Proc. Natl. Acad. Sci. USA 81:3655–3659.

(List continued on next page.)

*Primary Examiner*—Rebecca E. Prouty
*Assistant Examiner*—Sheridan L Swope

(57) ABSTRACT

Novel human polynucleotide and polypeptide sequences are disclosed that can be used in therapeutic, diagnostic, and pharmacogenomic applications.

5 Claims, No Drawings

OTHER PUBLICATIONS

Lowy et al, 1980, "Isolation of Transforming DNA: clonig the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recommbinant antibodies processing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligoeoxynucleotides", Nucleic Acid Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of Chimaeri processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vetors", PRoc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted form *Escherichia coli*", Nature 341:544–546.

Wigler et al, 1977, "Transfer of Purified Herpes Virus Thymidine Kinase to Cultured Mouse Cells", 11:223–232.

Wigler et al, 1980, "Transformation mammalian cells with an amplifiable dominant–acting gene", Proc. Natl. Acad. Sci. USA 77(6):3567–3570.

\* cited by examiner

SEQUENCE LISTING

<160> NUMBER OF SEQ ID NOS: 5

<210> SEQ ID NO 1
<211> LENGTH: 1476
<212> TYPE: DNA
<213> ORGANISM: homo sapiens

<400> SEQUENCE: 1

| | | | | | |
|---|---|---|---|---|---|
| atgaagcccc | gcgcgcgcgg | atggcggggc | ttggcggcgc | tgtggatgct | gttggcgcag     60 |
| gtggccgagc | aggcacctgc | gtgcgccatg | ggacccgcag | cggcagcgcc | tgggagcccg    120 |
| agcgtcccgc | gtcctcctcc | acccgcggag | cggccgggct | ggatggaaaa | gggcgaatat    180 |
| gacctggtct | ctgcctacga | ggttgaccac | agggggcgatt | acgtgtccca | tgaaatcatg    240 |
| caccatcagc | ggcggagaag | agcagtggcc | gtgtccgagg | ttgagtctct | tcaccttcgg    300 |
| ctgaaaggct | ccaggcacga | cttccacgtg | gatctgagga | cttccagcag | cctagtggct    360 |
| cctggcttta | ttgtgcagac | gttgggaaag | acaggcacta | agtctgtgca | gactttaccg    420 |
| ccagaggact | tctgtttcta | tcaaggctct | ttgcgatcac | acagaaactc | ctcagtggcc    480 |
| ctttcaacct | gccaaggctt | gtcaggcatg | atacgaacag | aagaggcaga | ttacttccta    540 |
| aggccacttc | cttcacacct | ctcatggaaa | ctcggcagag | ctgcccaagg | cagctcgcca    600 |
| tcccacgtac | tgtacaagag | atccacagag | ccccatgctc | ctggggccag | tgaggtcctg    660 |
| gtgacctcaa | ggacatggga | gctggcacat | caaccccctgc | acagcagcga | ccttcgcctg    720 |
| ggactgccac | aaaagcagca | tttctgtgga | agacgcaaga | aatacatgcc | ccagcctccc    780 |
| aaggaagacc | tcttcatctt | gccagatgag | tataagtctt | gcttacggca | taagcgctct    840 |
| cttctgaggt | cccatagaaa | tgaagaactg | aacgtggaga | ccttggtggt | ggtcgacaaa    900 |
| aagatgatgc | aaaaccatgg | ccatgaaaat | atcaccacct | acgtgctcac | gatactcaac    960 |
| atggtatctg | ctttattcaa | agatggaaca | ataggaggaa | acatcaacat | tgcaattgta   1020 |
| ggtctgattc | ttctagaaga | tgaacagcca | ggactggtga | taagtcacca | cgcagaccac   1080 |
| accttaagta | gcttctgcca | gtggcagtct | ggattgatgg | ggaaagatgg | gactcgtcat   1140 |
| gaccacgcca | tcttactgac | tggtctggat | atatgttcct | ggaagaatga | gccctgtgac   1200 |
| actttgggat | ttgcacccat | aagtggaatg | tgtagtaaat | atcgcagctg | cacgattaat   1260 |
| gaagatacag | gtcttggact | ggccttcacc | attgcccatg | agtctggaca | caactttggc   1320 |
| atgattcatg | atggagaagg | gaacatgtgt | aaaaagtccg | agggcaacat | catgtcccct   1380 |
| acattggcag | gacgcaatgg | agtcttctcc | tggtcaccct | gcagccgcca | gtatctacac   1440 |
| aaatttctaa | gatcagtgaa | aatgccagct | ctctga     |            |              1476 |

<210> SEQ ID NO 2
<211> LENGTH: 491
<212> TYPE: PRT
<213> ORGANISM: homo sapiens

<400> SEQUENCE: 2

Met Lys Pro Arg Ala Arg Gly Trp Arg Gly Leu Ala Ala Leu Trp Met
 1               5                  10                  15

Leu Leu Ala Gln Val Ala Glu Gln Ala Pro Ala Cys Ala Met Gly Pro
            20                  25                  30

Ala Ala Ala Ala Pro Gly Ser Pro Ser Val Pro Arg Pro Pro Pro Pro
        35                  40                  45

-continued

```
Ala Glu Arg Pro Gly Trp Met Glu Lys Gly Glu Tyr Asp Leu Val Ser
     50                  55                  60

Ala Tyr Glu Val Asp His Arg Gly Asp Tyr Val Ser His Glu Ile Met
 65                  70                  75                  80

His His Gln Arg Arg Arg Ala Val Ala Val Ser Glu Val Glu Ser
             85                  90                  95

Leu His Leu Arg Leu Lys Gly Ser Arg His Asp Phe His Val Asp Leu
             100                 105                 110

Arg Thr Ser Ser Ser Leu Val Ala Pro Gly Phe Ile Val Gln Thr Leu
             115                 120                 125

Gly Lys Thr Gly Thr Lys Ser Val Gln Thr Leu Pro Pro Glu Asp Phe
     130                 135                 140

Cys Phe Tyr Gln Gly Ser Leu Arg Ser His Arg Asn Ser Ser Val Ala
145                 150                 155                 160

Leu Ser Thr Cys Gln Gly Leu Ser Gly Met Ile Arg Thr Glu Glu Ala
                 165                 170                 175

Asp Tyr Phe Leu Arg Pro Leu Pro Ser His Leu Ser Trp Lys Leu Gly
             180                 185                 190

Arg Ala Ala Gln Gly Ser Ser Pro Ser His Val Leu Tyr Lys Arg Ser
         195                 200                 205

Thr Glu Pro His Ala Pro Gly Ala Ser Glu Val Leu Val Thr Ser Arg
     210                 215                 220

Thr Trp Glu Leu Ala His Gln Pro Leu His Ser Ser Asp Leu Arg Leu
225                 230                 235                 240

Gly Leu Pro Gln Lys Gln His Phe Cys Gly Arg Arg Lys Lys Tyr Met
                 245                 250                 255

Pro Gln Pro Pro Lys Glu Asp Leu Phe Ile Leu Pro Asp Glu Tyr Lys
             260                 265                 270

Ser Cys Leu Arg His Lys Arg Ser Leu Leu Arg Ser His Arg Asn Glu
             275                 280                 285

Glu Leu Asn Val Glu Thr Leu Val Val Asp Lys Lys Met Met Gln
     290                 295                 300

Asn His Gly His Glu Asn Ile Thr Thr Tyr Val Leu Thr Ile Leu Asn
305                 310                 315                 320

Met Val Ser Ala Leu Phe Lys Asp Gly Thr Ile Gly Gly Asn Ile Asn
                 325                 330                 335

Ile Ala Ile Val Gly Leu Ile Leu Leu Glu Asp Glu Gln Pro Gly Leu
             340                 345                 350

Val Ile Ser His His Ala Asp His Thr Leu Ser Ser Phe Cys Gln Trp
         355                 360                 365

Gln Ser Gly Leu Met Gly Lys Asp Gly Thr Arg His Asp His Ala Ile
     370                 375                 380

Leu Leu Thr Gly Leu Asp Ile Cys Ser Trp Lys Asn Glu Pro Cys Asp
385                 390                 395                 400

Thr Leu Gly Phe Ala Pro Ile Ser Gly Met Cys Ser Lys Tyr Arg Ser
                 405                 410                 415

Cys Thr Ile Asn Glu Asp Thr Gly Leu Gly Leu Ala Phe Thr Ile Ala
             420                 425                 430

His Glu Ser Gly His Asn Phe Gly Met Ile His Asp Gly Glu Gly Asn
         435                 440                 445

Met Cys Lys Lys Ser Glu Gly Asn Ile Met Ser Pro Thr Leu Ala Gly
     450                 455                 460

Arg Asn Gly Val Phe Ser Trp Ser Pro Cys Ser Arg Gln Tyr Leu His
```

```
                                    465                 470                 475                 480
                            Lys Phe Leu Arg Ser Val Lys Met Pro Ala Leu
                                                485                 490

<210> SEQ ID NO 3
<211> LENGTH: 3675
<212> TYPE: DNA
<213> ORGANISM: homo sapiens

<400> SEQUENCE: 3
atgaagcccc  gcgcgcgcgg  atggcggggc  ttggcggcgc  tgtggatgct  gctggcgcag    60
gtggccgagc  aggcacctgc  gtgcgccatg  ggacccgcag  cggcagcgcc  tgggagcccg   120
agcgtcccgc  gtcctcctcc  acccgcggag  cggccgggct  ggatggaaaa  gggcgaatat   180
gacctggtct  ctgcctacga  ggttgaccac  agggcgatt   acgtgtccca  tgaaatcatg   240
caccatcagc  ggcggagaag  agcagtggcc  gtgtccgagg  ttgagtctct  tcaccttcgg   300
ctgaaaggct  ccaggcacga  cttccacgtg  gatctgagga  cttccagcag  cctagtggct   360
cctggcttta  ttgtgcagac  gttgggaaag  acaggcacta  agtctgtgca  gacttttaccg  420
ccagaggact  tctgtttcta  tcaaggctct  ttgcgatcac  acagaaactc  ctcagtggcc   480
ctttcaacct  gccaaggctt  gtcaggcatg  atacgaacga  agaggcaga   ttacttccta   540
aggccacttc  cttcacacct  ctcatggaaa  ctcggcagag  ctgcccaagg  cagctcgcca   600
tcccacgtac  tgtacaagag  atccacagag  ccccatgctc  ctggggccag  tgaggtcctg   660
gtgacctcaa  ggacatggga  gctggcacat  caaccctgc   acagcagcga  ccttcgcctg   720
ggactgccac  aaaagcagca  tttctgtgga  agacgcaaga  aatacatgcc  ccagcctccc   780
aaggaagacc  tcttcatctt  gccagatgag  tataagtctt  gcttacggca  taagcgctct   840
cttctgaggt  cccatagaaa  tgaagaactg  aacgtggaga  ccttggtggt  ggtcgacaaa   900
aagatgatgc  aaaaccatgg  ccatgaaaat  atcaccacct  acgtgctcac  gatactcaac   960
atggtatctg  ctttattcaa  agatggaaca  ataggaggaa  acatcaacat  tgcaattgta  1020
ggtctgattc  ttctagaaga  tgaacagcca  ggactggtga  taagtcacca  cgcagaccac  1080
accttaagta  gcttctgcca  gtggcagtct  ggattgatgg  ggaaagatgg  gactcgtcat  1140
gaccacgcca  tcttactgac  tggtctggat  atatgttcct  ggaagaatga  gccctgtgac  1200
actttgggat  tgcacccat   aagtggaatg  tgtagtaaat  atcgcagctg  cacgattaat  1260
gaagatacag  gtcttggact  ggccttcacc  attgcccatg  agtctggaca  caactttggc  1320
atgattcatg  atggagaagg  gaacatgtgt  aaaaagtccg  agggcaacat  catgtcccct  1380
acattggcag  gacgcaatgg  agtcttctcc  tggtcaccct  gcagccgcca  gtatctacac  1440
aaatttctaa  gcaccgctca  agctatctgc  cttgctgatc  agccaaagcc  tgtgaaggaa  1500
tacaagtatc  tgagaaatt   gccaggagaa  ttatatgatg  caaacacaca  gtgcaagtgg  1560
cagttcggag  agaaagccaa  gctctgcatg  ctggacttta  aaaggacat   ctgtaaagcc  1620
ctgtggtgcc  atcgtattgg  aaggaaatgt  gagactaaat  ttatgccagc  agcagaaggc  1680
acaatttgtg  ggcatgacat  gtggtgccgg  ggaggacagt  gtgtgaaata  tggtgatgaa  1740
ggcccccaag  ccacccatgg  ccactggtcg  actggtcctt  cttggtcccc  atgctccagg  1800
acctgcggag  ggggagtatc  tcataggagt  cgcctctgca  ccaacccaa   gccatcgcat  1860
ggagggaagt  tctgtgaggg  ctccactcgc  actctgaagc  tctgcaacag  tcagaaatgt  1920
ccccgggaca  gtgttgactt  ccgtgctgct  cagtgtgccg  agcacaacag  cagacgattc  1980
```

-continued

| | | | | |
|---|---|---|---|---|
| agagggcggc | actacaagtg | gaagccttac | actcaagtag | aagatcagga cttatgcaaa | 2040 |
| ctctactgta | tcgcagaagg | atttgatttc | ttcttttctt | tgtcaaataa agtcaaagat | 2100 |
| gggactccat | gctcggagga | tagccgtaat | gtttgtatag | atgggatatg tgagagagtt | 2160 |
| ggatgtgaca | atgtccttgg | atctgatgct | gttgaagacg | tctgtggggt gtgtaacggg | 2220 |
| aataactcag | cctgcacgat | tcacaggggt | ctctacacca | agcaccacca caccaaccag | 2280 |
| tattatcaca | tggtcaccat | tccttctgga | gcccggagta | tccgcatcta tgaaatgaac | 2340 |
| gtctctacct | cctacatttc | tgtgcgcaat | gccctcagaa | ggtactacct gaatgggcac | 2400 |
| tggaccgtgg | actggcccgg | ccggtacaaa | ttttcgggca | ctactttcga ctacagacgg | 2460 |
| tcctataatg | agcccgagaa | cttaatcgct | actggaccaa | ccaacgagac actgattgtg | 2520 |
| gagctgctgt | tcagggaag | gaacccgggt | gttgcctggg | aatactccat gcctcgcttg | 2580 |
| gggaccgaga | agcagccccc | tgcccagccc | agctacactt | gggccatcgt gcgctctgag | 2640 |
| tgctccgtgt | cctgcggagg | gggacagatg | accgtgagag | agggctgcta cagagacctg | 2700 |
| aagtttcaag | taaatatgtc | cttctgcaat | cccaagacac | gacctgtcac ggggctggtg | 2760 |
| ccttgcaaag | tatctgcctg | tcctcccagc | tggtccgtgg | ggaactggag tgcctgcagt | 2820 |
| cggacgtgtg | gcggggtgc | ccagagccgc | cccgtgcagt | gcacgcgcg ggtgcactat | 2880 |
| gactcggagc | cagtcccggc | cagcctgtgc | cctcagcctg | ctccctccag caggcaggcc | 2940 |
| tgcaactctc | agagctgccc | acctgcatgg | agcgccgggc | cctgggcaga gtgctcacac | 3000 |
| acctgtggga | aggggtggag | gaagcgggca | gtggcctgta | agagcaccaa cccctcggcc | 3060 |
| agagcgcagc | tgctgcccga | cgctgtctgc | acctccgagc | ccaagcccag gatgcatgaa | 3120 |
| gcctgtctgc | ttcagcgctg | ccacaagccc | aagaagctgc | agtggctggt gtccgcctgg | 3180 |
| tcccagtgct | ctgtgacatg | tgaaagagga | acacagaaaa | gattcttaaa atgtgctgaa | 3240 |
| aagtatgttt | ctggaaagta | tcgagagctg | gcctcaaaga | agtgctcaca tttgccgaag | 3300 |
| cccagcctgg | agctggaacg | tgcctgcgcc | ccgcttccat | gccccaggca cccccattt | 3360 |
| gctgctgcgg | gaccctcgag | gggcagctgg | tttgcctcac | cctggtctca gtgcacggcc | 3420 |
| agctgtgggg | gaggcgttca | gacgaggtcc | gtgcagtgcc | tggctggggg ccggccggcc | 3480 |
| tcaggctgcc | tcctgcacca | gaagccttcg | gcctccctgg | cctgcaacac tcacttctgc | 3540 |
| cccattgcag | agaagaaaga | tgccttctgc | aaagactact | tccactggtg ctacctggta | 3600 |
| ccccagcacg | ggatgtgcag | ccacaagttc | tacggcaagc | agtgctgcaa gacttgctct | 3660 |
| aagtccaact | tgtga | | | | 3675 |

<210> SEQ ID NO 4
<211> LENGTH: 1224
<212> TYPE: PRT
<213> ORGANISM: homo sapiens

<400> SEQUENCE: 4

Met Lys Pro Arg Ala Arg Gly Trp Arg Gly Leu Ala Ala Leu Trp Met
 1               5                  10                  15

Leu Leu Ala Gln Val Ala Glu Gln Ala Pro Ala Cys Ala Met Gly Pro
            20                  25                  30

Ala Ala Ala Ala Pro Gly Ser Pro Ser Val Pro Arg Pro Pro Pro
        35                  40                  45

Ala Glu Arg Pro Gly Trp Met Glu Lys Gly Glu Tyr Asp Leu Val Ser
    50                  55                  60

Ala Tyr Glu Val Asp His Arg Gly Asp Tyr Val Ser His Glu Ile Met

-continued

```
 65                  70                  75                  80
His His Gln Arg Arg Arg Ala Val Ala Val Ser Glu Val Glu Ser
                85                  90                  95
Leu His Leu Arg Leu Lys Gly Ser Arg His Asp Phe His Val Asp Leu
            100                 105                 110
Arg Thr Ser Ser Ser Leu Val Ala Pro Gly Phe Ile Val Gln Thr Leu
            115                 120                 125
Gly Lys Thr Gly Thr Lys Ser Val Gln Thr Leu Pro Pro Glu Asp Phe
130                 135                 140
Cys Phe Tyr Gln Gly Ser Leu Arg Ser His Arg Asn Ser Ser Val Ala
145                 150                 155                 160
Leu Ser Thr Cys Gln Gly Leu Ser Gly Met Ile Arg Thr Glu Glu Ala
            165                 170                 175
Asp Tyr Phe Leu Arg Pro Leu Pro Ser His Leu Ser Trp Lys Leu Gly
            180                 185                 190
Arg Ala Ala Gln Gly Ser Ser Pro Ser His Val Leu Tyr Lys Arg Ser
            195                 200                 205
Thr Glu Pro His Ala Pro Gly Ala Ser Glu Val Leu Val Thr Ser Arg
            210                 215                 220
Thr Trp Glu Leu Ala His Gln Pro Leu His Ser Ser Asp Leu Arg Leu
225                 230                 235                 240
Gly Leu Pro Gln Lys Gln His Phe Cys Gly Arg Arg Lys Lys Tyr Met
            245                 250                 255
Pro Gln Pro Pro Lys Glu Asp Leu Phe Ile Leu Pro Asp Glu Tyr Lys
            260                 265                 270
Ser Cys Leu Arg His Lys Arg Ser Leu Leu Arg Ser His Arg Asn Glu
            275                 280                 285
Glu Leu Asn Val Glu Thr Leu Val Val Asp Lys Lys Met Met Gln
            290                 295                 300
Asn His Gly His Glu Asn Ile Thr Thr Tyr Val Leu Thr Ile Leu Asn
305                 310                 315                 320
Met Val Ser Ala Leu Phe Lys Asp Gly Thr Ile Gly Gly Asn Ile Asn
            325                 330                 335
Ile Ala Ile Val Gly Leu Ile Leu Glu Asp Glu Gln Pro Gly Leu
            340                 345                 350
Val Ile Ser His His Ala Asp His Thr Leu Ser Ser Phe Cys Gln Trp
            355                 360                 365
Gln Ser Gly Leu Met Gly Lys Asp Gly Thr Arg His Asp His Ala Ile
            370                 375                 380
Leu Leu Thr Gly Leu Asp Ile Cys Ser Trp Lys Asn Glu Pro Cys Asp
385                 390                 395                 400
Thr Leu Gly Phe Ala Pro Ile Ser Gly Met Cys Ser Lys Tyr Arg Ser
            405                 410                 415
Cys Thr Ile Asn Glu Asp Thr Gly Leu Gly Leu Ala Phe Thr Ile Ala
            420                 425                 430
His Glu Ser Gly His Asn Phe Gly Met Ile His Asp Gly Glu Gly Asn
            435                 440                 445
Met Cys Lys Lys Ser Glu Gly Asn Ile Met Ser Pro Thr Leu Ala Gly
            450                 455                 460
Arg Asn Gly Val Phe Ser Trp Ser Pro Cys Ser Arg Gln Tyr Leu His
465                 470                 475                 480
Lys Phe Leu Ser Thr Ala Gln Ala Ile Cys Leu Ala Asp Gln Pro Lys
            485                 490                 495
```

```
Pro Val Lys Glu Tyr Lys Tyr Pro Glu Lys Leu Pro Gly Glu Leu Tyr
            500                 505                 510

Asp Ala Asn Thr Gln Cys Lys Trp Gln Phe Gly Glu Lys Ala Lys Leu
            515                 520                 525

Cys Met Leu Asp Phe Lys Lys Asp Ile Cys Lys Ala Leu Trp Cys His
            530                 535                 540

Arg Ile Gly Arg Lys Cys Glu Thr Lys Phe Met Pro Ala Ala Glu Gly
545                 550                 555                 560

Thr Ile Cys Gly His Asp Met Trp Cys Arg Gly Gly Gln Cys Val Lys
            565                 570                 575

Tyr Gly Asp Glu Gly Pro Lys Pro Thr His Gly His Trp Ser Asp Trp
            580                 585                 590

Ser Ser Trp Ser Pro Cys Ser Arg Thr Cys Gly Gly Gly Val Ser His
            595                 600                 605

Arg Ser Arg Leu Cys Thr Asn Pro Lys Pro Ser His Gly Gly Lys Phe
            610                 615                 620

Cys Glu Gly Ser Thr Arg Thr Leu Lys Leu Cys Asn Ser Gln Lys Cys
625                 630                 635                 640

Pro Arg Asp Ser Val Asp Phe Arg Ala Ala Gln Cys Ala Glu His Asn
            645                 650                 655

Ser Arg Arg Phe Arg Gly Arg His Tyr Lys Trp Lys Pro Tyr Thr Gln
            660                 665                 670

Val Glu Asp Gln Asp Leu Cys Lys Leu Tyr Cys Ile Ala Glu Gly Phe
            675                 680                 685

Asp Phe Phe Phe Ser Leu Ser Asn Lys Val Lys Asp Gly Thr Pro Cys
            690                 695                 700

Ser Glu Asp Ser Arg Asn Val Cys Ile Asp Gly Ile Cys Glu Arg Val
705                 710                 715                 720

Gly Cys Asp Asn Val Leu Gly Ser Asp Ala Val Glu Asp Val Cys Gly
            725                 730                 735

Val Cys Asn Gly Asn Asn Ser Ala Cys Thr Ile His Arg Gly Leu Tyr
            740                 745                 750

Thr Lys His His His Thr Asn Gln Tyr Tyr His Met Val Thr Ile Pro
            755                 760                 765

Ser Gly Ala Arg Ser Ile Arg Ile Tyr Glu Met Asn Val Ser Thr Ser
            770                 775                 780

Tyr Ile Ser Val Arg Asn Ala Leu Arg Tyr Tyr Leu Asn Gly His
785                 790                 795                 800

Trp Thr Val Asp Trp Pro Gly Arg Tyr Lys Phe Ser Gly Thr Thr Phe
            805                 810                 815

Asp Tyr Arg Arg Ser Tyr Asn Glu Pro Glu Asn Leu Ile Ala Thr Gly
            820                 825                 830

Pro Thr Asn Glu Thr Leu Ile Val Glu Leu Leu Phe Gln Gly Arg Asn
            835                 840                 845

Pro Gly Val Ala Trp Glu Tyr Ser Met Pro Arg Leu Gly Thr Glu Lys
            850                 855                 860

Gln Pro Pro Ala Gln Pro Ser Tyr Thr Trp Ala Ile Val Arg Ser Glu
865                 870                 875                 880

Cys Ser Val Ser Cys Gly Gly Gly Gln Met Thr Val Arg Glu Gly Cys
            885                 890                 895

Tyr Arg Asp Leu Lys Phe Gln Val Asn Met Ser Phe Cys Asn Pro Lys
            900                 905                 910
```

-continued

Thr Arg Pro Val Thr Gly Leu Val Pro Cys Lys Val Ser Ala Cys Pro
        915                 920                 925
Pro Ser Trp Ser Val Gly Asn Trp Ser Ala Cys Ser Arg Thr Cys Gly
        930                 935                 940
Gly Gly Ala Gln Ser Arg Pro Val Gln Cys Thr Arg Arg Val His Tyr
945                 950                 955                 960
Asp Ser Glu Pro Val Pro Ala Ser Leu Cys Pro Gln Pro Ala Pro Ser
                965                 970                 975
Ser Arg Gln Ala Cys Asn Ser Gln Ser Cys Pro Pro Ala Trp Ser Ala
        980                 985                 990
Gly Pro Trp Ala Glu Cys Ser His Thr Cys Gly Lys Gly Trp Arg Lys
        995                 1000                1005
Arg Ala Val Ala Cys Lys Ser Thr Asn Pro Ser Ala Arg Ala Gln Leu
        1010                1015                1020
Leu Pro Asp Ala Val Cys Thr Ser Glu Pro Lys Pro Arg Met His Glu
1025                1030                1035                1040
Ala Cys Leu Leu Gln Arg Cys His Lys Pro Lys Lys Leu Gln Trp Leu
                1045                1050                1055
Val Ser Ala Trp Ser Gln Cys Ser Val Thr Cys Glu Arg Gly Thr Gln
        1060                1065                1070
Lys Arg Phe Leu Lys Cys Ala Glu Lys Tyr Val Ser Gly Lys Tyr Arg
        1075                1080                1085
Glu Leu Ala Ser Lys Lys Cys Ser His Leu Pro Lys Pro Ser Leu Glu
        1090                1095                1100
Leu Glu Arg Ala Cys Ala Pro Leu Pro Cys Pro Arg His Pro Pro Phe
1105                1110                1115                1120
Ala Ala Ala Gly Pro Ser Arg Gly Ser Trp Phe Ala Ser Pro Trp Ser
                1125                1130                1135
Gln Cys Thr Ala Ser Cys Gly Gly Gly Val Gln Thr Arg Ser Val Gln
        1140                1145                1150
Cys Leu Ala Gly Gly Arg Pro Ala Ser Gly Cys Leu Leu His Gln Lys
        1155                1160                1165
Pro Ser Ala Ser Leu Ala Cys Asn Thr His Phe Cys Pro Ile Ala Glu
        1170                1175                1180
Lys Lys Asp Ala Phe Cys Lys Asp Tyr Phe His Trp Cys Tyr Leu Val
1185                1190                1195                1200
Pro Gln His Gly Met Cys Ser His Lys Phe Tyr Gly Lys Gln Cys Cys
                1205                1210                1215
Lys Thr Cys Ser Lys Ser Asn Leu
        1220

<210> SEQ ID NO 5
<211> LENGTH: 4042
<212> TYPE: DNA
<213> ORGANISM: homo sapiens

<400> SEQUENCE: 5
ccttcccgcg ctctgcttgg gtcgggtcct ccctgcccgc tcgcacgctg ccggccgggg      60
accctccggt ggcccctagc ccctcggagc gctcctggat gaagcccgc gcgcgcggat     120 ggcggggctt ggcggcgctg tgatgctgc tggcgcaggt ggccgagcag gcacctgcgt     180
gcgccatggg acccgcagcg gcagcgcctg ggagcccgag cgtcccgcgt cctcctccac     240
ccgcggagcg gccgggctgg atggaaaagg gcgaatatga cctggtctct gcctacgagg     300
ttgaccacag gggcgattac gtgtcccatg aaatcatgca ccatcagcgg cggagaagag     360

-continued

```
cagtggccgt gtccgaggtt gagtctcttc accttcggct gaaaggctcc aggcacgact    420
tccacgtgga tctgaggact tccagcagcc tagtggctcc tggctttatt gtgcagacgt    480
tgggaaagac aggcactaag tctgtgcaga ctttaccgcc agaggacttc tgtttctatc    540
aaggctcttt gcgatcacac agaaactcct cagtggccct ttcaacctgc caaggcttgt    600
caggcatgat acgaacagaa gaggcagatt acttcctaag gccacttcct tcacacctct    660
catggaaact cggcagagct gcccaaggca gctcgccatc ccacgtactg tacaagagat    720
ccacagagcc ccatgctcct ggggccagtg aggtcctggt gacctcaagg acatgggagc    780
tggcacatca cccctgcac agcagcgacc ttcgcctggg actgccacaa agcagcatt    840 tctgtggaag acgcaagaaa tacatgcccc agcctcccaa ggaagacctc ttcatcttgc    900
cagatgagta taagtcttgc ttacggcata gcgctctct tctgaggtcc catagaaatg    960
aagaactgaa cgtggagacc ttggtggtgg tcgacaaaaa gatgatgcaa aaccatggcc    1020
atgaaaatat caccacctac gtgctcacga tactcaacat ggtatctgct ttattcaaag    1080
atggaacaat aggaggaaac atcaacattg caattgtagg tctgattctt ctagaagatg    1140
aacagccagg actggtgata agtcaccacg cagaccacac cttaagtagc ttctgccagt    1200
ggcagtctgg attgatgggg aaagatggga ctcgtcatga ccacgccatc ttactgactg    1260
gtctggatat atgttcctgg aagaatgagc cctgtgacac tttgggattt gcacccataa    1320
gtggaatgtg tagtaaatat cgcagctgca cgattaatga agatacaggt cttggactgg    1380
ccttcaccat tgcccatgag tctggacaca actttggcat gattcatgat ggagaaggga    1440
acatgtgtaa aaagtccgag gcaacatca tgtccctac attggcagga cgcaatggag    1500
tcttctcctg gtcaccctgc agccgccagt atctacacaa atttctaagc accgctcaag    1560
ctatctgcct tgctgatcag ccaaagcctg tgaaggaata caagtatcct gagaaattgc    1620
caggagaatt atatgatgca aacacacagt gcaagtggca gttcggagag aaagccaagc    1680
tctgcatgct ggactttaaa aaggacatct gtaaagccct gtggtgccat cgtattggaa    1740
ggaaatgtga gactaaattt atgccagcag cagaaggcac aatttgtggg catgacatgt    1800
ggtgccgggg aggacagtgt gtgaaatatg gtgatgaagg ccccaagccc acccatggcc    1860
actggtcgga ctggtcttct tggtccccat gctccaggac ctgcggaggg ggagtatctc    1920
ataggagtcg cctctgcacc aaccccaagc catcgcatgg agggaagttc tgtgagggct    1980
ccactcgcac tctgaagctc tgcaacagtc agaaatgtcc ccgggacagt gttgacttcc    2040
gtgctgctca gtgtgccgag cacaacagca gacgattcag agggcggcac tacaagtgga    2100
agccttacac tcaagtagaa gatcaggact tatgcaaact ctactgtatc gcagaaggat    2160
ttgatttctt ctttttcttt g tcaaataaag tcaaagatgg gactccatgc tcggaggata    2220
gccgtaatgt ttgtatagat gggatatgtg agagagttgg atgtgacaat gtccttggat    2280
ctgatgctgt tgaagacgtc tgtggggtgt gtaacgggaa taactcagcc tgcacgattc    2340 acagggtct ctacaccaag caccaccaca ccaaccagta ttatcacatg gtcaccattc    2400
cttctggagc ccggagtatc cgcatctatg aaatgaacgt ctctacctcc tacatttctg    2460
tgcgcaatgc cctcagaagg tactacctga atgggcactg gaccgtggac tggcccggcc    2520
ggtacaaatt ttcgggcact actttcgact acagacggtc ctataatgag cccgagaact    2580
taatcgctac tggaccaacc aacgagacac tgattgtgga gctgctgttt cagggaagga    2640
acccgggtgt tgcctgggaa tactccatgc ctcgcttggg gaccgagaag cagcccctg    2700
```

-continued

| | | | | | |
|---|---|---|---|---|---|
| cccagcccag | ctacacttgg | gccatcgtgc | gctctgagtg | ctccgtgtcc | tgcggagggg | 2760 |
| gacagatgac | cgtgagagag | ggctgctaca | gagacctgaa | gtttcaagta | aatatgtcct | 2820 |
| tctgcaatcc | caagacacga | cctgtcacgg | ggctggtgcc | ttgcaaagta | tctgcctgtc | 2880 |
| ctcccagctg | gtccgtgggg | aactggagtg | cctgcagtcg | gacgtgtggc | gggggtgccc | 2940 |
| agagccgccc | cgtgcagtgc | acacggcggg | tgcactatga | ctcggagcca | gtcccggcca | 3000 |
| gcctgtgccc | tcagcctgct | ccctccagca | ggcaggcctg | caactctcag | agctgcccac | 3060 |
| ctgcatggag | cgccgggccc | tgggcagagt | gctcacacac | ctgtgggaag | gggtggagga | 3120 |
| agcgggcagt | ggcctgtaag | agcaccaacc | cctcggccag | agcgcagctg | ctgcccgacg | 3180 |
| ctgtctgcac | ctccgagccc | aagcccagga | tgcatgaagc | ctgtctgctt | cagcgctgcc | 3240 |
| acaagcccaa | gaagctgcag | tggctggtgt | ccgcctggtc | ccagtgctct | gtgacatgtg | 3300 |
| aaagaggaac | acagaaaaga | ttcttaaaat | gtgctgaaaa | gtatgtttct | ggaaagtatc | 3360 |
| gagagctggc | ctcaaagaag | tgctcacatt | tgccgaagcc | cagcctggag | ctggaacgtg | 3420 |
| cctgcgcccc | gcttccatgc | cccaggcacc | ccccatttgc | tgctgcggga | ccctcgaggg | 3480 |
| gcagctggtt | tgcctcaccc | tggtctcagt | gcacggccag | ctgtggggga | ggcgttcaga | 3540 |
| cgaggtccgt | gcagtgcctg | gctgggggcc | ggccggcctc | aggctgcctc | ctgcaccaga | 3600 |
| agccttcggc | ctccctggcc | tgcaacactc | acttctgccc | cattgcagag | aagaaagatg | 3660 |
| ccttctgcaa | agactacttc | cactggtgct | acctggtacc | ccagcacggg | atgtgcagcc | 3720 |
| acaagttcta | cggcaagcag | tgctgcaaga | cttgctctaa | gtccaacttg | tgagttggga | 3780 |
| ccgctctccg | tagcagagaa | agtgcctgcg | tggcacagaa | atttcccaca | aatgagctgt | 3840 |
| gcaatctacg | tcggaataca | tccaaggaag | agcaaagcca | aaagaagaaa | accgtgttag | 3900 |
| gctctttgac | caggagtgta | tgtatgtgtt | tcactgtgag | cctgggtgca | gacctgtgtc | 3960 |
| cccatgcaca | cagtgtctcc | tgtcaggctg | aaatgtggca | ccctggcaga | cagagctgtg | 4020 |
| gctcgtgagg | cagaaggcag | gc | | | | 4042 |

HUMAN PROTEASES AND POLYNUCLEOTIDES ENCODING THE SAME

The present application claims the benefit of U.S. Provisional Application Number 60/225,852 which was filed on Aug. 16, 2000 and is herein incorporated by reference in its entirety.

1. INTRODUCTION

The present invention relates to the discovery, identification, and characterization of novel human polynucleotides encoding proteins sharing sequence similarity with mammalian proteases. The invention encompasses the described polynucleotides, host cell expression systems, the encoded proteins, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed polynucleotides that can be used for diagnosis, drug screening, clinical trial monitoring, or the treatment of physiological disorders or diseases.

2. BACKGROUND OF THE INVENTION

Proteases cleave protein substrates as part of degradation, maturation, and secretory pathways within the body. Proteases have been associated with, inter alia, regulating development, diabetes, obesity, infertility, modulating cellular processes, and infectious disease.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal proteases and particularly zinc metalloproteases.

The novel human nucleic acid (cDNA) sequences described herein, encode proteins/open reading frames (ORFs) of 491 and 1224 amino acids in length (see SEQ ID NOS: 2 and 4 respectively).

The invention also encompasses agonists and antagonists of the described NHPs, including small molecules, large molecules, mutant NHPs, or portions thereof that compete with native NHPs, NHP peptides, and antibodies, as well as nucleotide sequences that can be used to inhibit the expression of the described NHPs (e.g., antisense and ribozyme molecules, and gene or regulatory sequence replacement constructs) or to enhance the expression of the described NHPs (e.g., expression constructs that place the described gene under the control of a strong promoter system), and transgenic animals that express a NHP transgene, or "knockouts" (which can be conditional) that do not express a functional NHP.

Further, the present invention also relates to processes for identifying compounds that modulate, i.e., act as agonists or antagonists, of NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of several NHP ORFs encoding the described NHP amino acid sequences. SEQ ID NO:5 describes a NHP ORF and flanking sequences.

5. DETAILED DESCRIPTION OF THE INVENTION

The NHPs described for the first time herein are novel proteins that are expressed in, inter alia, human cell lines, and human fetal brain, brain, pituitary, cerebellum, spinal cord, thymus, lymph node, trachea, kidney, fetal liver, prostate, testis, thyroid, adrenal gland, pancreas, small intestine, colon, skeletal muscle, heart, uterus, mammary gland, adipose, esophagus, bladder, cervix, pericardium, ovary, fetal kidney, and fetal lung cells.

The described sequences were compiled from cDNA clones, genomic sequence, and cDNAs derived from human kidney, mammary gland, and cerebellum mRNAs (Edge Biosystems, Gaithersburg, Md., and Clontech, Palo Alto, Calif.). The present invention encompasses the nucleotides presented in the Sequence Listing, host cells expressing such nucleotides, the expression products of such nucleotides, and: (a) nucleotides that encode mammalian homologs of the described genes, including the specifically described NHPs, and NHP products; (b) nucleotides that encode one or more portions of a NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF), or a contiguous exon splice junction first described in the Sequence Listing, that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or a NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. In yet another embodiment, the antisense oligonucleotide is an a-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or nonhuman cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, AP-NHP or NHP-AP fusion proteins. In cases where a NHP mutation results in an expressed gene product with altered function (e.g., as a result of a missense or a frameshift mutation), polyclonal antibodies to NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation) or genetically engineered transcription factor. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, regulatable, viral (particularly retroviral LTR promoters) the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast a-mating factors.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHPs or NHP peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics a NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and corresponding deduced amino acid sequences of the described NHPs are presented in the Sequence Listing. SEQ ID NO:5 describes a NHP ORF as well as flanking regions. The NHP nucleotides were obtained from human cDNA libraries using probes and/or primers generated from human genomic sequence. Expression analysis has provided evidence that the described NHP can be expressed a variety of human cells.

5.2 NHPS AND NHP POLYPEPTIDES

The NHPs, NHP polypeptides, NHP peptide fragments, mutated, truncated, or deleted forms of NHP, and/or NHP fusion proteins can be prepared for a variety of uses, including but not limited to the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and disease. The described NHPs share similarity with a variety of proteases, including proteases having thrombospondin repeats, disintegrins, aggrecanases, and metalloproteinases (especially zinc metalloproteases of the ADAMTS family).

The Sequence Listing discloses the amino acid sequences encoded by the described NHP polynucleotides. The NHPs display an initiator methionines in DNA sequence contexts consistent with a translation initiation site, and several of the ORFs display a signal-like sequence which can indicate that the described NHP ORFs are secreted proteins or can be membrane associated.

The NHP amino acid sequences of the invention include the amino acid sequences presented in the Sequence Listing as well as analogues and derivatives thereof. Further, corresponding NHP homologues from other species are encompassed by the invention. In fact, any NHPs encoded by a NHP nucleotide sequence described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biolog", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, a NHP peptide or NHP polypeptide is thought to be a soluble or secreted molecule, the peptide or polypeptide can be recovered from the culture media. Such expression systems also encompass engineered host cells that express NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of a NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP encoding nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the NHP product being expressed. For example, when a large quantity of such a protein is to be produced for the generation of pharmaceutical compositions of and/or containing a NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP gene coding sequence can be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a NHP product. Such engineered cell lines may be particularly useful in screening and evaluation of compounds that affect the endogenous activity of a NHP product.

A number of selection systems may be used, including but not limited to the herpes simplex virus thymidine kinase (Wigler, et al., 1977, Cell 11:223), hypoxanthineguanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci.

USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$nitriloacetic acid-agarose columns and histidine-tagged proteins are selectively eluted with imidazole-containing buffers.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of a NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of a NHP), truncated NHP polypeptides (NHP in which one or more domains have been deleted), functional equivalents of a NHP or mutated variants of a NHP. Such host animals may include but are not limited to pigs, rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc.

Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:127–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J. 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" a NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence encoding an amino acid sequence drawn from the group consisting of SEQ ID NOS: 2 and 4.

2. An isolated nucleic acid molecule comprising a nucleotide sequence that:
   (a) encodes the amino acid sequence shown in SEQ ID NO: 4; and
   (b) hybridizes under stringent conditions of hybridization to filter-bound DNA in 0.5 M NaHPO$_4$, 7% SDS, 1mM EDT at 65° C. and washing in 0.1×SSC/1% SDS at 68° C. to the nucleotide sequence of SEQ ID NO: 3 or the complement thereof.

3. An isolated nucleic acid molecule according to claim 1 wherein said nucleotide sequence is present in cDNA.

4. An isolated nucleic acid molecule encoding the amino acid sequence presented in SEQ ID NO:4.

5. An isolated nucleic acid molecule encoding the amino acid sequence presented in SEQ ID NO:2.

* * * * *